United States Patent [19]

Rivier et al.

[11] Patent Number: 4,728,726

[45] Date of Patent: * Mar. 1, 1988

[54] GRF ANALOGS IIIB

[75] Inventors: Jean E. F. Rivier; Wylie W. Vale, Jr., both of La Jolla, Calif.

[73] Assignee: The Salk Institute for Biological Studies, San Diego, Calif.

[*] Notice: The portion of the term of this patent subsequent to May 21, 2002 has been disclaimed.

[21] Appl. No.: 939,342

[22] Filed: Dec. 8, 1986

Related U.S. Application Data

[63] Continuation of Ser. No. 736,180, May 20, 1986, abandoned, which is a continuation-in-part of Ser. No. 432,663, Oct. 4, 1982, Pat. No. 4,563,352, which is a continuation-in-part of Ser. No. 457,862, Jan. 13, 1983, Pat. No. 4,529,595, which is a continuation-in-part of Ser. No. 488,748, Apr. 26, 1983, Pat. No. 4,595,676, which is a continuation-in-part of Ser. No. 532,170, Sep. 13, 1983, abandoned, which is a continuation-in-part of Ser. No. 545,094, Oct. 25, 1983, Pat. No. 4,518,586, which is a continuation-in-part of Ser. No. 611,844, May 18, 1984, Pat. No. 4,525,190.

[51] Int. Cl.$^4$ .............................................. C07K 7/10
[52] U.S. Cl. .................................................... 530/324
[58] Field of Search ............................ 514/12; 530/324

[56] References Cited

U.S. PATENT DOCUMENTS

| | | | |
|---|---|---|---|
| 4,518,586 | 5/1985 | Rivier et al. | 514/12 |
| 4,525,190 | 7/1985 | Vale, Sr. et al. | 514/12 |
| 4,529,595 | 7/1985 | Rivier et al. | 514/12 |
| 4,563,352 | 1/1986 | Rivier et al. | 514/12 |
| 4,585,756 | 4/1986 | Brazeau, Jr. et al. | 514/12 |

Primary Examiner—Delbert R. Phillips
Attorney, Agent, or Firm—Fitch, Even, Tabin & Flannery

[57] ABSTRACT

Human GRF(hGRF), rat GRF(rGRF), porcine GRF(pGRF), ovine GRF(oGRF) and bovine GRF(bGRF) have been earlier characterized and synthesized. The invention provides synthetic peptides which are extremely potent in stimulating the release of pituitary GH in animals, including humans, which have resistance to enzymatic degradation in the body, and which contain the sequence: $R_1$-$R_2$-$R_3$-Ala-Ile-Phe-Thr-$R_8$-Ser-$R_{10}$-Arg-$R_{12}$-$R_{13}$-$R_{14}$-$R_{15}$-Gln-$R_{17}$-$R_{18}$-Ala-Arg-Lys-Leu-$R_{23}$-$R_{24}$-$R_{25}$-Ile-$R_{27}$-$R_{28}$-$R_{29}$-$R_{30}$-$R_{31}$-$R_{32}$, wherein $R_1$ is Tyr, D-Tyr, Met, Phe, D-Phe, pCl-Phe, Leu, His or D-His having either a $C^a$Me or $N^a$Me substitution or being unsubstituted; $R_2$ is Ala, D-Ala or D-NMA; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{14}$ is Leu or D-Leu, $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, Asp, D-Glu or D-Asp; $R_{27}$ is Met, D-Met, Ala, Nle, Ile, Leu, Nva or Val; $R_{28}$ is Asn, Ser or des$R_{28}$; $R_{29}$ is Arg, D-Arg or des$R_{29}$; $R_{30}$ is Gln or des$R_{30}$; $R_{31}$ is Glu or des$R_{31}$; and $R_{32}$ is Gly or des$R_{32}$. These peptides as well as their nontoxic salts may also be used diagnostically.

25 Claims, No Drawings

GRF ANALOGS IIIB

This invention was made with Government support under Grant AM-26741 awarded by the National Institutes of Health. The Government has certain rights in this invention.

This application is a continuation of our copending application Ser. No. 736,180, filed May 20, 1986, now abandoned which was a continuation-in-part of our earlier copending applications Ser. Nos. 432,663, filed Oct. 4, 1982 U.S. Pat. Nos. 4,563,352 Jan. 7, 1986; 457,862, filed Jan. 13, 1983 U.S. Pat. Nos. 4,529,595 July 15, 1985; 488,748, filed Apr. 26, 1983 U.S. Pat. Nos. 4,595,676 June 17, 1986; 532,170, filed Sept. 13, 1983 abandoned; 545,094, filed Oct. 25, 1983 U.S. Pat. No. 4,518,586 May 21, 1985 and 611,844, filed May 18, 1984 U.S. Pat. No. 4,525,190 July 9, 1985.

The present invention relates to peptides having influence on the function of the pituitary gland in humans and other animals. In particular, the present invention is directed to a peptide which promotes the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. A hypothalamic inhibitory factor was characterized in 1972 in the form of somatostatin which inhibits the secretion of growth hormone(GH). In 1982, human pancreatic (tumor) releasing factors (hpGRF) were isolated from extracts of human pancreatic tumors, purified, characterized, synthesized and tested, which were found to promote the release of GH by the pituitary. Both of these hypophysiotropic factors have been reproduced by total synthesis, and analogs of the native structures have been synthesized. It is believed that human hypothalamic GH releasing factor has precisely the same structure; thus the term hGRF is used hereinafter. A corresponding rat hypothalamic GH releasing factor(rGRF), a corresponding porcine hypothalamic GH releasing factor(pGRF) and a corresponding bovine hypothalamic GH releasing factor(bGRF) have also been characterized and synthesized.

SUMMARY OF THE INVENTION

Synthetic polypeptides have now been synthesized and tested which release GH from cultured pituitary cells and which may at least partially resist enzymatic degradation in the body and exhibit very substantially increased potency. These peptides may contain 44 or even more amino acid residues; however, they preferably have a sequence containing 32 or fewer residues and which may be as short as 27 residues. These peptides may have various substitutions for the residues which appear in a natural GRF sequence, such as D-Ala or $N^\alpha CH_3$-D-Ala(D-NMA) in the 2-position, D-Tyr in the 10-position, D-Leu in the 14-position, D-Ala in the 15-position, Nle in the 27-position, Asn in the 28-position, D-Arg in the 29-position, D-Leu in the 17-and/or 23-positions, and either D-Glu or D-Asp in the 25-position. The peptides may also have one of the following 15 residues in the 1-position: Tyr, D-Tyr, Met, Phe, D-Phe, pCl-Phe, Leu, His and D-His, which residue may optionally have a methyl substitution either on the alpha-carbon or in the alpha-amino group. They may optionally have D-Asp at the 3-position and/or either D-Arg or D-Ser at the 8-position and/or D-Tyr at the 10-position and/or D-Ala at the 15-position. They may also have D-Met or Nva instead of either Nle or Met in the 27-position; however, an L-isomer is preferred in the shorter analogs.

Pharmaceutical compositions in accordance with the invention include such analogs which are between about 27 and 44 residues in length, or a nontoxic salt of any of these, dispersed in a pharmaceutically or veterinarily acceptable liquid or solid carrier. Such pharmaceutical compositions can be used in clinical medicine, both human and veterinary, for administration for therapeutic purposes, and also diagnostically. Moreover, they can be used to promote the growth of warm-blooded animals, including fowl, and in aquiculture for cold-blooded animals, e.g. fish, eels, etc.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminus appears to the left and the carboxyl group at the C-terminus to the right. By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. Where the amino acid residue has isomeric forms, it is the L-form of the amino acid that is represented unless otherwise expressly indicated. D-NMA signifies the D-isomer of alanine wherein the alpha-amino group is substituted by methyl.

The invention provides synthetic peptides having the following formula (I): $R_1$-$R_2$-$R_3$-Ala-Ile-Phe-Thr-$R_8$-Ser-$R_{10}$-Arg-$R_{12}$-$R_{13}$-$R_{14}$-$R_{15}$-Gln-$R_{17}$-$R_{18}$-Ala-Arg-Lys-Leu-$R_{23}$-$R_{24}$-$R_{25}$-Ile-$R_{27}$-$R_{28}$-$R_{29}$-$R_{30}$-$R_{31}$-$R_{32}$-Y wherein $R_1$ is Tyr, D-Tyr, Met, Phe, D-Phe, pCl-Phe, Leu, His or D-His having either a $C^\alpha Me$ or $N^\alpha Me$ substitution or being unsubstituted; $R_2$ is Ala, D-Ala or D-NMA; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{14}$ is Leu or D-Leu; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, Asp, D-Glu or D-Asp; $R_{27}$ is Met, D-Met, Ala, Nle, Ile, Leu, Nva or Val; $R_{28}$ is Asn, Ser or des$R_{28}$; $R_{29}$ is Arg, D-Arg or des$R_{29}$; $R_{30}$ is Gln or des$R_{30}$; $R_{31}$ is Gln or des$R_{31}$; $R_{32}$ is Gly or des$R_{32}$; and Y represents the carboxyl moiety of the amino acid residue at the C-terminus of the sequence and may be any of the following radicals: —COOR,—CRO,—CONHNHR,—CON(R)(R') or —CH$_2$OR, with R and R' being lower alkyl, fluoro lower alkyl or hydrogen; methyl, ethyl and propyl are the preferred lower alkyl groups. When Met appears in position 1, it is preferable to have another residue in position 27. When D-NMA is present in the 2-position, an L-isomer is preferably present in the 1-position.

As defined above, peptides which extend from the N-terminus through residue-27 have biological potency in effecting the release of GH by the pituitary, and such biologically active fragments are considered as falling within the scope of the overall invention. When the peptide extends only to residue 27 or 28, Y should be —CONH$_2$ or a substituted amide. When the peptide extends to one of residues 29 thru 32, Y is preferably an amide. When the peptide has 40 or more residues, there is no clear preference for the moiety at the C-terminus.

The peptides are synthesized by a suitable method, such as by exclusively solid-phase techniques, by partial solid-phase techniques, by fragment condensation or by classical solution couplings. The employment of recently developed recombinant DNA techniques may be used to prepare a portion of an analog containing only natural amino acid residues, which could then be linked to a short N-terminal peptide. For example, techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula (II): $X^1$-$R_1$(X or $X^2$)-$R_2$-$R_3$($X^3$)-Ala-Ile-Phe-Thr($X^4$)-$R_8$($X^4$ or $X^5$)-Ser($X^4$)-$R_{10}$($X^2$)-Arg($X^6$)-$R_{12}$($X^6$ or $X^7$)-$R_{13}$-$R_{14}$-$R_{15}$-Gln($X^5$)-$R_{17}$-$R_{18}$($X^2$)-Ala-Arg($X^6$)-Lys($X^7$)-Leu-$R_{23}$-$R_{24}$(X or $X^5$)-$R_{25}$($X^3$)-Ile-$R_{27}$-$R_{28}$($X^4$ or $X^5$)-$R_{29}$($X^6$)-$R_{30}$($X^5$)-$R_{31}$($X^5$)-$R_{32}$-$X^8$ wherein: $X^1$ is either hydrogen or an a-amino protecting group. The a-amino protecting groups contemplated by $X^1$ are those well known to be useful in the art of step-wise synthesis of polypeptides. Among the classes of a-amino protecting groups which may be employed as $X^1$ are (1) aromatic urethan-type protecting groups, such as fluorenylmethyloxycarbonyl (FMOC), benzyloxycarbonyl(Z) and substituted Z, such as p-chlorobenzyloxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (BOC), diisopropylmethyloxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. The preferred a-amino protecting group is BOC, even when an $N^a$Me-substituted residue is employed in the 1-position.

X is hydrogen or a protecting group for the imidazole nitrogen of His, such as Tos.

$X^2$ may be a suitable protecting group for the phenolic hydroxyl group of Tyr, such as tetrahydropyranyl, tert-butyl, trityl, Bzl, CBZ, 4Br-CBZ and 2,6-dichlorobenzyl(DCB). The preferred protecting group is 2,6-dichlorobenzyl. $X^2$ can be hydrogen which means that there is no side-chain protecting group on the amino acid residue in that position.

$X^3$ is hydrogen or a suitable ester-forming protecting group for the carboxyl group of Asp or Glu, such as benzyl(OBzl), 2,6-dichlorobenzyl, methyl and ethyl.

$X^4$ may be a suitable protecting group for the hydroxyl group of Thr or Ser, such as acetyl, benzoyl, tert-butyl, trityl, tetrahydropyranyl, Bzl, 2,6-dichlorobenzyl and CBZ. The preferred protecting group is Bzl. $X^4$ can be hydrogen, which means there is no protecting group on the hydroxyl group.

$X^5$ is hydrogen or a suitable protecting group for the side chain amido group of Asn or Gln. It is preferably xanthyl(Xan).

$X^6$ is a suitable protecting group for the guanidino group of Arg, such as nitro, Tos, CBZ, adamantyloxycarbonyl, and BOC, or is hydrogen.

$X^7$ is hydrogen or a suitable protecting group for the side chain amino group of Lys. Illustrative of suitable side chain amino protecting groups are 2-chlorobenzyloxycarbonyl(2-Cl-Z), Tos, t-amyloxycarbonyl and BOC.

Met, if present, can optionally be protected by oxygen, but is preferably left unprotected.

The selection of a side chain amino protecting group is not critical except that generally one is chosen which is not removed during deprotection of the a-amino groups during the synthesis. However, for some amino acids, e.g. His, protection is not generally necessary after coupling is completed, and the protecting groups may be the same.

$X^8$ is a suitable protecting group for the C-terminal carboxyl group, such as the ester-forming group $X^3$, or is an anchoring bond used in solid-phase synthesis for linking to a solid resin support, or is des-$X^8$, in which case the residue at the C-terminal has a carboxyl moiety which is Y, as defined hereinbefore. When a solid resin support is used, it may be any of those known in the art, such as one having the formulae: —O—$CH_2$-resin support, —NH-benzhydrylamine (BHA) resin support, -NH-paramethylbenzhydrylamine (MBHA) resin support or an N-alkylaminomethyl resin (NAAM resin). When the unsubstituted amide is desired, use of BHA or MBHA resin is preferred, because cleavage directly gives the amide. In case the N-methyl amide is desired, it can be generated from an N-methyl BHA resin; other substituted amides can be synthesized using an NAAM resin. Should groups other than the free acid be desired at the C-terminus, it may be preferable to sythesize the peptide using classical methods as set forth in the Houben-Weyl text.

In the formula for the intermediate, at least one of the X-groups is a protecting group or $X^8$ includes resin support. Thus, the invention also provides a method for manufacturing a peptide of interest by (a) forming a peptide having at least one protecting group and the formula (II): wherein: X, $X^1$, $X^2$, $X^3$, $X^4$, $X^5$, $X^6$, and $X^7$ are each either hydrogen or a protecting group and $X^8$ is either a protecting group or an anchoring bond to resin support or is des-$X^8$, in which case the residue at the C-terminus has a carboxy moiety which is Y; (b) splitting off the protecting group or groups or anchoring bond from the peptide of the formula (II); and (c) if desired, converting the resulting peptide of the formula (I) into a nontoxic salt thereof.

In selecting a particular side chain protecting group to be used in the synthesis of the peptides, the following general rules are followed: (a) the protecting group preferably retains its protecting properties and is not be split off under coupling conditions, (b) the protecting group should be stable to the reagent and, with the exception of Xan, is preferably stable under the reaction conditions selected for removing the a-amino protecting group at each step of the synthesis, and (c) the side chain protecting group must be removable, upon the completion of the synthesis containing the desired amino acid sequence, under reaction conditions that will not undesirably alter the peptide chain.

When peptides are not prepared using recombinant DNA technology, they are preferably prepared using solid phase synthesis, such as that generally described by Merrifield, *J. Am. Chem. Soc.*, 85, p 2149 (1963), although other equivalent chemical syntheses known in the art can also be used as previously mentioned. Solid-phase synthesis is commenced from the C-terminus of the peptide by coupling a protected a-amino acid to a suitable resin. Such a starting material can be prepared by attaching an a-amino-protected amino acid by an ester linkage to a chloromethylated resin or a hydroxymethyl resin, by an amide bond to a BHA resin or MBHA resin, or by a substituted amide linkage to an NAAM resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6. BHA and MBHA resin supports are commercially available and are generally used only when the desired polypeptide being synthesized has an unsubstituted amide at the C-terminal. The preparation of NAAM resins is described in detail in copending U.S. Pat. Application Ser. No. 545,077, filed Oct. 24, 1983, the disclosure of which is incorporated herein by reference.

The C-terminal amino acid, e.g. Asn, protected by BOC and by Xan, can be first coupled to the chloromethylated resin according to the procedure set forth in *Chemistry Letters*, K. Horiki et al. 165-168 (1978), using KF in DMF at about 60° C. for 24 hours with stirring, when the 43-residue peptide is to be synthesized. Following the coupling of the BOC-protected amino acid to the resin support, the a-amino protecting group is removed, as by using trifluoroacetic acid(TFA) in methylene chloride or TFA alone. The deprotection is carried out at a temperature between about 0° C. and room temperature. Other standard cleaving reagents, such as HCl in dioxane, and conditions for removal of specific a-amino protecting groups may be used as described in Schroder & Lubke, "The Peptides", 1 pp 72-75 (Academic Press 1965).

After removal of the a-amino protecting group, the remaining a-amino- and side chain-protected amino acids are coupled stepwise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke supra, in Chapter III and by Kapoor, *J. Phar. Sci.*, 59, pp 1-27 (1970).

Each protected amino acid or amino acid sequence is introduced into the solid phase reactor in about a fourfold or more excess, and the coupling may be carried out in a medium of dimethylformamide(DMF): $CH_2Cl_2$ (1:1) or in DMF or $CH_2Cl_2$ alone. In cases where incomplete coupling occurs, the coupling procedure is repeated before removal of the a-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp 1927-1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups X, $X^2$, $X^3$, $X^4$, $X^5$, $X^6$ and $X^7$ and the anchoring bond and also the a-amino protecting group $X^1$ if one is used, to obtain the peptide in the form of the free acid. If Met is present in the sequence, the BOC protecting group is preferably first removed using trifluoroacetic acid(TFA)/ethanedithiol prior to cleaving the peptide from the resin with HF to eliminate potential S-alkylation. When using hydrogen fluoride for cleaving, anisole and methylethyl sulfide are included as scavengers in the reaction vessel.

The following Example sets forth a preferred method for synthesizing peptides by the solid-phase technique. It will of course be appreciated that the synthesis of a correspondingly shorter peptide fragment is effected in the same manner by merely eliminating the requisite number of amino acids at either end of the chain; however, it is presently felt that biologically active fragments should contain the indicated sequence at the N-terminus.

EXAMPLE I

The synthesis of the peptide [D-$NMA^2$, D-$Asn^{28}$]-rGRF(1-43)-OH having the formula: His-D-NMA-Asp-Ala-Ile-Phe-Thr-Ser-Ser-Tyr-Arg-Arg-Ile-Leu-Gly-Gln-Leu-Tyr-Ala-Arg-Lys-Leu-Leu-His-Glu-Ile-Met-D-Asn-Arg-Gln-Gln-Gly-Glu-Arg-Asn-Gln-Glu-Gln-Arg-Ser-Arg-Phe-Asn-OH is conducted in a stepwise manner using a Beckman 990 peptide synthesizer on a chloromethylated resin having a substitution range of about 0.1 to 0.5 mmoles/g. resin. Coupling of BOC-Asn(Xan) to the resin is performed by the general procedure set forth in *Chemistry Letters*, supra, using KF in DMF at about 60° C. for 24 hours with stirring, and it results in the substitution of about 0.35 mmol. Asn per gram of resin.

After deblocking and neutralization, the peptide chain is built step-by-step on the resin. Deblocking, neutralization and addition of each amino acid is performed in general accordance with the procedure set forth in detail in Rivier, J, *J. Amer. Chem. Soc.*, 96, 2986-2992 (1974). All solvents that are used are carefully degassed by sparging with an inert gas, e.g. helium or nitrogen, to insure the absence of oxygen that might undesirably oxidize the sulfur of the Met residue.

Deblocking is preferably carried out in accordance with Schedule A which follows:

| SCHEDULE A | |
|---|---|
| Reagent | Mixing time (Min.) |
| 1. 60% TFA/2% ethanedithiol | 10 |
| 2. 60% TFA/2% ethanedithiol | 15 |
| 3. IPA/1% ethanedithiol | 0.5 |
| 4. Et$_3$N (10%) in CH$_2$Cl$_2$ | 0.5 |
| 5. MeOH | 0.5 |
| 6. Et$_3$N (10%) in CH$_2$Cl$_2$ | 0.5 |
| 7. MeOH (twice) | 0.5 |
| 8. CH$_2$Cl$_2$ (twice) | 0.5 |

The couplings are preferably carried out as set out in Schedule B which follows:

| SCHEDULE B | |
|---|---|
| Reagent | Mixing time (Min.) |
| 9. DCCI | — |
| 10. Boc-amino acid | 50-90 |
| 11. MeOH (twice) | 0.5 |
| 12. CH$_2$Cl$_2$ (twice) | 0.5 |
| 13. Ac$_2$O (3 M) in CH$_2$Cl$_2$ | 15.0 |
| 14. CH$_2$Cl$_2$ | 0.5 |
| 15. MeOH | 0.5 |
| 16. CH$_2$Cl$_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(TOS) is being coupled, a mixture of 50% DMF and methylene chloride is used. Bzl ether is used as the hydroxyl side chain protecting group for Ser and Thr. The amido group of Asn and Gln is protected by Xan when DCC coupling is used as is preferred. P-nitrophenyl ester(ONp) may also be used to activate the carboxyl end of Asn or Gln, and for example, BOC-Asn(ONp) can be coupled overnight using one equivalent of HOBt in a 50% mixture of DMF and methylene chloride, in which case no DCC is added. 2-chloro-benzyloxycarbonyl(2Cl-Z) is used as the protecting group for the Lys side chain. Tos is used to protect the guanidino group of Arg and the imidazole nitrogen of His, and the Glu or Asp sidechain carboxyl group is protected with OBzl. The phenolic hydroxyl group of Tyr is protected with 2,6-dichlorobenzyl(DCB). At the end of the synthesis, the following composition is obtained: BOC-His(X)-D-NMA-Asp(X$^3$)-Ala-Ile-Phe-Thr(X$^4$)-Ser(X$^4$)-Ser(X$^4$)-Tyr(X$^2$)-Arg(X$^6$)-Arg(X$^6$)-Ile-Leu-Gly-Gln(X$^5$)-Leu-Tyr(X$^2$)-Ala-Arg(X$^6$)-Lys(X$^7$)-Leu-Leu-His(X)-Glu(X$^3$)-Ile-Met-D-Asn(X$^5$)-Arg(X$^6$)-Gln(X$^5$)-Gln(X$^5$)-Gly-Glu(X$^3$)-Arg(X$^6$)-Asn(X$^5$)-Gln(X$^5$)-Glu(X$^3$)-Gln(X$^5$)-Arg(X$^6$)-Ser(X$^4$)-Arg(X$^6$)-Phe-Asn(X$^5$)-X$^8$ wherein X is Tos, X$^2$ is DCB, X$^3$ is OBzl, X$^4$ is Bzl, X$^5$ is Xan, X$^6$ is Tos, X$^7$ is 2Cl-Z and X$^8$ is —O—CH$_2$-resin support. Xan may have been partially or totally removed by TFA treatment used to deblock the a-amino protecting group.

In order to cleave and deprotect the protected peptide-resin, it is treated with 1.5 ml. anisole, 0.5 ml. methylethylsulfide and 15 ml. hydrogen fluoride(HF) per gram of peptide-resin, at −20° C. for one-half hour and at 0.° C. for one-half hour. After elimination of the HF under high vacuum, the resin-peptide remainder is washed alternately with dry diethyl ether and chloroform, and the peptide is then extracted with degassed 2N aqueous acetic acid and separated from the resin by filtration.

The cleaved and deprotected peptide is then dissolved in 0-5% acetic acid and subjected to purification which may include Sephadex G-50 fine gel filtration.

The peptide is then further purified by preparative or semi-preparative HPLC as described in Rivier et al., *Peptides: Structure and Biological Function,* (1979) pp 125-8 and Marki et al. *J. Am. Chem. Soc.* 103, 3178 (1981). Cartridges fitting Waters Associates prep LC-500 are packed with 15–20 $\mu$C$_{18}$ Silica from Vydac (300A). A gradient of CH$_3$CN in TEAP is generated by a low pressure Eldex gradient maker, as described in Rivier, J., *J. Liq. Chromatography* 1, 343–367 (1978). The chromatographic fractions are carefully monitored by HPLC, and only the fractions showing substantial purity are pooled. Desalting of the purified fractions, independently checked for purity, is achieved using a gradient of CH$_3$CN in 0.1% TFA. The center cut is then lyophilized to yield the desired peptide, the purity of which can be greater than 98%.

The synthesis is repeated using an MBHA resin to produce the same peptide having an amidated C-terminus using an initial procedure as generally described in Vale et al. U.S. Pat. No. 4,292,313 to link Asn to the MBHA resin.

EXAMPLE II

The synthesis of a 44-residue amidated peptide [His$^1$, D-NMA$^2$, D-Tyr$^{10}$, Nle$^{27}$]-hGRF(1-44)-NH$_2$ having the formula: H-His-D-NMA-Asp-Ala-Ile-Phe-Thr-Asn-Ser-D-Tyr-Arg-Lys-Val-Leu-Gly-Gln-Leu-Ser-Ala-Arg-Lys-Leu-Leu-Gln-Asp-Ile-Nle-Ser-Arg-Gln-Gln-Gly-Glu-Ser-Asn-Gln-Glu-Arg-Gly-Ala-Arg-Ala-Arg-Leu-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE III

The synthesis of [D-Ala$^2$, Nle$^{27}$]-rGRF(1-29)-NH$_2$ having the formula: H-His-D-Ala-Asp-Ala-Ile-Phe-Thr-Ser-Ser-Tyr-Arg-Arg-Ile-Leu-Gly-Gln-Leu-TYyr-Ala-Arg-Lys-Leu-Leu-His-Glu-Ile-Nle-Asn-Arg-NH$_2$ is conducted in a stepwise manner using a Beckman 990 Peptide Synthesizer in the manner generally described in Example II. The peptide is judged to be substantially pure using TLC and HPLC.

EXAMPLE IV

The synthesis of the hGRF analog, [D-NMA$^2$, Nle$^{27}$, Asn$^{28}$]-hGRF(1-29)-NHEt having the formula: H-Tyr-D-NMA-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Asn-Arg-NHCH$_2$CH$_3$ is conducted in a stepwise manner using a Beckman 990 Peptide Synthesizer generally as in Example I but employing an N-alkylamine resin, specifically an N-ethylaminomethyl resin (NEAM resin), as described in copending U.S. patent application Ser. No. 545,077 filed Oct. 24, 1983 in the name of W. D. Kornreich et al., the disclosure of which is incorporated herein by reference. About 10 grams of the chloromethylated resin of Example I are reacted with 100 ml. of ethylamine at about 4° C. for about 24 hours with continuous stirring to change the a-chlorobenzyl groups to N-ethyl a-aminobenzyl groups, upon which the peptide is then built via an initial, substituted-amide linkage.

Upon completion of the desired peptide sequence, deprotection and cleavage from the resin is effected by treatment with HF, with anisole as a scavenger, stirring first at 0° C. and then allowing the stirred mixture to slowly warm to room temperature over about 3 hours, a procedure which cleaves the peptide from the resin as the ethylamide. Amino acid analysis shows that the desired peptide structure is obtained. This analog is judged to be substantially pure using TLC and HPLC.

EXAMPLE V

The synthesis of the hGRF analog [D-Ala$^2$, Nle$^{27}$, Asn$^{28}$]-hGRF(1-29)-NHEt having the formula: H-Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Asn-Arg-NHCH$_2$CH$_3$ is conducted in a stepwise manner using a Beckman 990 Peptide Synthesizer on an NEAM resin as in Example IV. The peptide is judged to be substantially pure using TLC and HPLC.

EXAMPLE VI

The synthesis of [D-NMA$^2$, Ser$^{18}$, Nle$^{27}$]-rGRF (1-29)-NH$_2$, having the formula: H-His-D-NMA-Asp-Ala-Ile-Phe-Thr-Ser-Ser-Tyr-Arg-Arg-Ile-Leu-Gly-Gln-Leu-Ser-Ala-Arg-Lys-Leu-Leu-His-Glu-Ile-Nle-Asn-Arg-NH$_2$ is conducted in a stepwise manner using a Beckman 990 Peptide Synthesizer on an MBHA resin as in Example II. The peptide is judged to be substantially pure using TLC and HPLC.

The synthesis is repeated to produce [D-Ala$^2$, Ser$^{18}$, Nle$^{27}$]-rGRF(1-29)-NH$_2$.

EXAMPLE VII

The synthesis of [D-Ala$^2$, Nle$^{27}$]-hGRF(1-29)-NH$_2$ having the formula: H-Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$ is conducted in a stepwise manner using a Beckman 990 Peptide Synthesizer on an MBHA resin as in Example II. The peptide is judged to be substantially pure using TLC and HPLC.

EXAMPLE VIII

The synthesis of [D-NMA$^2$, D-Tyr$^{10}$, Nle$^{27}$]-rGRF (1-29)-NHEt having the formula: H-His-D-NMA-Asp-Ala-Ile-Phe-Thr-Ser-Ser-D-Tyr-Arg-Arg-Ile-Leu-Gly-Gln-Leu-Tyr-Ala-Arg-Lys-Leu-Leu-His-Glu-Ile-Nle-Asn-Arg-NHCH$_2$CH$_3$ is conducted in a stepwise manner using a Beckman 990 Peptide Synthesizer on an NEAM resin as in Example IV. The peptide is judged to be substantially pure using TLC and HPLC.

EXAMPLE IX

The synthesis of [His$^1$, D-NMA$^2$, Nle$^{27}$]-hGRF(1-29)-NHEt having the formula: H-His-D-NMA-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NHCH$_2$CH$_3$ is conducted in a stepwise manner using a Beckman 990 Peptide Synthesizer on an NEAM resin as in Example IV. The peptide is judged to be substantially pure using TLC and HPLC.

EXAMPLE X

The synthesis of [His$^1$, D-NMA$^2$, D-Tyr$^{10}$, Nle$^{27}$]-hGRF(1-29)-NHEt having the formula: H-His-D-NMA-Asp-Ala-Ile-Phe-Thr-Asn-Ser-D-Tyr-Arg-Lys-Val-Leu-Gly-Gln-Leu-Ser-Ala-Arg-Lys-Leu-Leu-Gln-Asp-Ile-Nle-Ser-Arg-NHCH$_2$CH$_3$ is conducted in a stepwise manner using a Beckman 990 Peptide Synthesizer on an NEAM resin as in Example IV. This analog is judged to be substantially pure using TLC and HPLC.

EXAMPLE XI

The synthesis of [D-Ala$^2$, D-Leu$^{23}$, Nle$^{27}$]-rGRF(1-43)-OH having the formula: H-His-D-Ala-Asp-Ala-Ile-Phe-Thr-Ser-Ser-Tyr-Arg-Arg-Ile-Leu-Gly-Gln-Leu-Tyr-Ala-Arg-Lys-Leu-D-Leu-His-Glu-Ile-Nle-Asn-Arg-Gln-Gln-Gly-Glu-Arg-Asn-Gln-Glu-Gln-Arg-Ser-Arg-Phe-Asn-OH is conducted in a stepwise manner using a Beckman 990 Peptide Synthesizer on a chloromethylated resin, in the manner generally described in Example I. The peptide is judged to be substantially pure using TLC and HPLC.

EXAMPLE XII

The synthesis of a rGRF analog i.e. [N$^a$MeTyr$^1$, D-NMA$^2$, Nle$^{27}$]-rGRF(1-29)-NH$_2$ having the formula: N$^a$MeTyr-D-NMA-Asp-Ala-Ile-Phe-Thr-Ser-Ser-Tyr-Arg-Arg-Ile-Leu-Gly-Gln-Leu-Tyr-Ala-Arg-Lys-Leu-Leu-His-Glu-Ile-Nle-Asn-Arg-NH$_2$ is conducted in a stepwise manner using a Beckman 990 Peptide Synthesizer on an MBHA resin as in Example II. The peptide is judged to be substantially pure using TLC and HPLC.

EXAMPLE XIII

The synthesis of [Nle$^{27}$]-hGRF(1-29)-NH$_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE XIV

The synthesis of [D-NMA$^2$, Nle$^{27}$, D-Asn$^{28}$]-hGRF (1-29)-NH$_2$ having the formula: H-Tyr-D-NMA-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-D-Asn-Arg-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE XV

The synthesis of [Nle$^{27}$, D-Asn$^{28}$]-rGRF(1-29)-NH$_2$ having the formula: H-His-Ala-Asp-Ala-Ile-Phe-Thr-Ser-Ser-Tyr-Arg-Arg-Ile-Leu-Gly-Gln-Leu-Tyr-Ala-Arg-Lys-Leu-Leu-His-Glu-Ile-Nle-D-Asn-Arg-NH$_2$ is conducted in a stepwise manner using a Beckman 990 Peptide Synthesizer on an MBHA resin as in Example II. The peptide is judged to be substantially pure using TLC and HPLC.

EXAMPLE XVI

The synthesis of [D-Ala$^2$, Nle$^{27}$]-rGRF (1-29)-NHEt, having the formula: H-His-D-Ala-Asp-Ala-Ile-Phe-Thr-Ser-Ser-Tyr-Arg-Arg-Ile-Leu-Gly-Gln-Leu-Tyr-Ala-Arg-Lys-Leu-His-Glu-Ile-Nle-Asn-Arg-NHCH$_2$CH$_3$ is conducted in a stepwise manner using a Beckman 990 Peptide Synthesizer on an NEAM resin as in Example IV. The peptide is judged to be substantially pure using TLC and HPLC.

EXAMPLE XVII

The synthesis of [D-Ala$^2$, Nle$^{27}$, Asn$^{28}$, D-Arg$^{29}$]-hGRF(1-29)-NHEt having the formula: H-Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Glu-Ile-Nle-Asn-D-Arg-NHCH$_2$CH$_3$ is conducted in a stepwise manner using a Beckman 990 Peptide Synthesizer on an NEAM resin as in Example IV. Following its removal from the resin and deprotection, the peptide is treated with 1 N acetic acid to produce the acetate salt thereof, prior to lyophilization. The peptide is judged to be substantially pure using TLC and HPLC.

EXAMPLE XVIII

The synthesis of the hGRF analog [D-Ala$^2$, D-Tyr$^{10}$, Nle$^{27}$]-hGRF(1-29)-NHEt having the formula: H-Tyr-D-Ala-Asp-Ala-Ile-Phe-Thr-Asn-Ser-D-Tyr-Arg-Lys-Val-Leu-Gly-Gln-Leu-Ser-Ala-Arg-Lys-Leu-Leu-Gln-Asp-Ile-Nle-Ser-Arg-NHCH$_2$CH$_3$ is conducted in a stepwise manner using a Beckman 990 Peptide Synthesizer on an NEAM resin as in Example IV. The peptide is judged to be substantially pure using TLC and HPLC.

EXAMPLE XIX

The synthesis of the hGRF analog [Nle$^{27}$]-hGRF(1-29)-NHEt having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NHCH$_2$CH$_3$ is conducted in a stepwise manner using a Beckman 990 Peptide Synthesizer on an NEAM resin as in Example IV. The peptide is judged to be substantially pure using TLC and HPLC.

The synthetic peptides prepared in the Examples are compared with synthetic hpGRF(1-40)-OH in in vitro assays and are found to exhibit generally greater potencies for the secretion of GH and similar intrinsic activities. All of these synthetic peptides are considered to be biologically active and potentially useful for stimulating the release of GH by the pituitary.

To determine the relative effectiveness of certain representative synthetic peptides to promote the release of growth hormone, in vitro assays are carried out using synthetic hpGRF(1-40)-OH as a standard in side-by-side comparison with equimolar concentrations of the representative analogs which have been synthesized. Cultures are used which include cells of rat pituitary glands removed some three to five days previously. Such cultures are considered optimal for the secretion of growth hormone and are used for the comparative testing, in the general manner described in Vale et al. *Endocrinology*, 91, 562–572 (1972) and as more particularly described in Vale et al. *Endocrinology*, 112, 1553–1555 (1983). Incubation with the substance to be tested is carried out for 3 to 4 hours, and aliquots of the culture medium are removed and processed to measure their contents in immunoreactive GH(ir GH) by a well-characterized radioimmunoassay.

The results of this comparative testing for equimolar concentrations are shown in Table I.

TABLE I

| Peptide | Comparison % |
| --- | --- |
| hGRF(1–40)-OH (standard for this test) | 100% |
| [D-NMA$^2$, Nle$^{27}$, Asn$^{28}$]-hGRF(1–29)-NHEt | 1805% |
| [D-Ala$^2$, Nle$^{27}$, Asn$^{28}$]-hGRF(1–29)-NHEt | 1714% |
| [His$^1$, D-NMA$^2$, Nle$^{27}$]-hGRF(1–29)-NHEt | 256% |
| [Nle$^{27}$]-hGRF(1–29)-NH$_2$ | 238% |
| [Nle$^{27}$, D-Asn$^{28}$]-rGRF(1–29)-NH$_2$ | 321% |
| [D-Ala$^2$, Nle$^{27}$]-hGRF(1–29)-NH$_2$ | 429% |
| [D-NMA$^2$, Ser$^{18}$, Nle$^{27}$]-rGRF(1–29)-NH$_2$ | 262% |

In vitro testing of these synthetic peptides shows that many of them have surprisingly greater biological potency than that exhibited by hpGRF(1-40)-OH, for example, the minimum effective concentration for [D-NMA$^2$, Nle$^{27}$, Asn$^{28}$]-hGRF(1-29)-NHEt is about 1 picomolar.

In addition to the in vitro tests for secretion of growth hormone, in vivo experiments inject the synthetic peptides intravenously into urethane-anesthetized male rats and determine that they suppress spontaneous GH secretion without abolishing the response to exogenous GRF. Blood samples are taken immediately prior to, and 10, 30 and 90 minutes after injections. GH levels in blood, measured by radioimmunoassay, show that synthetic [D-NMA$^2$, Nle$^{27}$, Asn$^{28}$]-hGRF(1-29)-NHEt is more than 6 times more potent than hGRF(1-40)-OH with respect to blood levels of pituitary GH when measured at both 10 and 30 min. after IV injection. Other known GRF in vivo tests that are known to be effective to detect secretion of GH are used to confirm these results. Dosages between about 50 nanograms and about 5 micrograms of these peptides per Kg. of body weight are considered to be effective in causing GH secretion. Some peptides which exhibit in vitro biological potency about equal to or even slightly less than the standard exhibit in vivo potency very much greater.

Such synthetic hGRF analogs and possibly rGRF, bGRF and pGRF analogs should be useful for human applications in which a physician wishes to elevate GH production. Stimulation of GH secretion by such analogs is of interest in patients with complete or relative GH deficiency caused by underproduction of endogenous GRF. Furthermore, it is probable that increased GH secretion and its attendant increase in growth could be obtained in humans or animals with normal GH levels. Moreover, administration should alter body fat content and modify other GH-dependent metabolic, immunologic and developmental processes. For example, these analogs may be useful as a means of stimulating anabolic processes in human beings under circumstances such as following the incurring of burns. As another example, these analogs may be administered to commercial warm-blooded animals, such as chickens, turkeys, pigs, goats, cattle and sheep, and may be used in aquiculture for raising fish and other cold-blooded marine animals, e.g. sea turtles and eels, and amphibians, to accelerate growth and increase the ratio of protein to fat gained by feeding effective amounts of the peptides.

For administration to humans, these synthetic peptides should have a purity of at least about 93% and preferably at least 98%. Purity, for purposes of this application, refers to the intended peptide constituting the stated weight % of all peptides and peptide fragments present. For the administration of such synthetic peptides to commercial and other animals in order to promote growth and reduce fat content, a purity as low as about 5%, or even as low as 0.01%, may be acceptable.

These synthetic peptides or the nontoxic salts thereof, combined with a pharmaceutically or veterinarily acceptable carrier to form a pharmaceutical composition, may be administered to animals, including humans, either intravenously, subcutaneously, intramuscularly, percutaneously, e.g. intranasally or even orally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically-acceptable carrier. Usually, the parenteral dosage will be from about 0.01 to about 1 microgram of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminus of the peptide and extending to about position-27, can be made in accordance with the known experimental practises to date to create peptides that retain all or very substantial portions of the biological potency of the peptide, and such peptides are considered as being within the scope of the invention. Moreover, additions may be made to either terminus, or to both termini, and/or generally equivalent residues can be substituted for naturally occurring residues, as is well-known in the overall art of peptide chemistry, to produce other analogs having at least a substantial portion of the potency of the claimed peptide without deviating from the scope of the invention. For example, all or any part of the peptide Glu-Ser-Asn-Gln-Glu-Arg-Gly-Ala-Arg-Ala-Arg-Leu can be added to $R_{32}$ in an analog of hGRF, and all or any part of the peptide Glu-Arg-Asn-Gln-Glu-Gln-Arg-Ser-Arg-Phe-Asn can be added to $R_{32}$ in an analog of rGRF. Moreover, modifications may be made to the preferred —NH$_2$ group at the C-terminus of the sequence in accordance with the state of this art today, for example, the carboxyl moiety of the amino acid residue at the C-terminus can be the radical —COOR, —CRO, —CONHNHR, —CON(R)(R') or —CH$_2$OR, with R and R' being lower alkyl, fluoro lower alkyl or hydrogen, without deviating from the invention for such modifications result in equivalent synthetic peptides.

Particular features of the invention are emphasized in the claims which follow.

What is claimed is:

1. A synthetic peptide, or a nontoxic salt thereof, having the amino acid residue sequence: $R_1$-$R_2$-$R_3$-Ala-Ile-Phe-Thr-$R_8$-Ser-$R_{10}$-Arg-$R_{12}$-$R_{13}$-$R_{14}$-$R_{15}$-Gln-$R_{17}$-$R_{18}$-Ala-Arg-Lys-Leu-$R_{23}$-$R_{24}$-$R_{25}$-Ile-$R_{27}$-$R_{28}$-$R_{29}$-$R_{30}$-$R_{31}$-$R_{32}$ wherein $R_1$ is Tyr, D-Tyr, Met, Phe, D-Phe, pCl-Phe, Leu, His or D-His having either a $C^a$Me or $N^a$Me substitution or being unsubstituted; $R_2$ is Ala, D-Ala or D-NMA; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{14}$ is Leu or D-Leu; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, Asp, D-Glu or D-Asp; $R_{27}$ is Met, D-Met, Ala, Nle, Ile, Leu, Nva or Val; $R_{28}$ is Asn, Ser, D-Asn or desR$_{28}$; $R_{29}$ is Arg, D-Arg or DesR$_{29}$; $R_{30}$ is Gln or [desGln] desR$_{30}$; $R_{31}$ is Gln or DesR$_{31}$; and $R_{32}$ is Gly or desR$_{32}$, provided however, that at least one of the following is present: $R_2$ is D-NMA; $R_{27}$ is Nle; $R_{28}$ is D-Asn.

2. The peptide of claim 1 wherein $R_2$ is D-NMA.

3. The peptide of claim 2 wherein $R_1$ is an L-isomer.

4. The peptide of claim 3 wherein the carboxyl moiety at the C-terminus of said sequence is-CONHR wherein R is hydrogen or ethyl.

5. The peptide of claim 1 which is [Nle$^{27}$]-hGRF(1-29)-NH$_2$.

6. The peptide of claim 1 which is [D-Ala$^2$, Nle$^{27}$]-hGRF(1-29)-NH$_2$.

7. The peptide of claim 1 which is [His$^1$, N-NMA$^2$, Nle$^{27}$]-hGRF(1-29)NHEt.

8. A synthetic peptide, or a nontoxic salt thereof, having the amino acid residue sequence: $R_1$-$R_2$-$R_3$-Ala-Ile-Phe-Thr-$R_8$-Ser-$R_{10}$-Arg-$R_{12}$-$R_{13}$-$R_{14}$-$R_{15}$-Gln-$R_{17}$-$R_{18}$-Ala-Arg-Lys-Leu-$R_{23}$-$R_{24}$-$R_{25}$-Ile-Nle-$R_{28}$-$R_{29}$-$R_{30}$-$R_{31}$-$R_{32}$ wherein $R_1$ is Tyr, D-Tyr, Met, Phe, D-Phe, pCl-phe, Leu, His or D-His having either a $C^a$Me or $N^a$Me substitution or being unsubstituted; $R_2$ is Ala, D-Ala or D-NMA; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{14}$ is Leu or D-Leu; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, Asp, D-Glu or D-Asp; [$R_{27}$ is Met, Ala, Nle, Ile, Leu, Nva or Val;] $R_{28}$ is Asn or D-Asn; $R_{29}$ is Arg or D-Arg; $R_{30}$ is Gln or desR$_{30}$; $R_{31}$ is Gln or desR$_{31}$; and $R_{32}$ is Gly or desR$_{32}$.

9. The peptide of claim 8 wherein $R_2$ is D-NMA.

10. The peptide of claim 9 wherein $R_1$ is an L-isomer.

11. The peptide of claim 10 wherein the carboxyl moiety at the C-terminus of said sequence is -13 CONHR and R is hydrogen or ethyl.

12. The peptide of claim 9 wherein $R_{28}$ is Asn.

13. The peptide of claim 12 wherein $R_{30}$ is desR$_{30}$, $R_{31}$ is desR$_{31}$ and $R_{32}$ is desR$_{32}$.

14. The peptide of claim 8 wherein $R_2$ is D-Ala.

15. The peptide of claim 14 wherein $R_1$ is an L-isomer.

16. The peptide of claim 15 wherein the carboxyl moiety at the C-terminus of said sequence is —CONHR wherein R is hydrogen or ethyl.

17. The peptide of claim 16 wherein $R_{28}$ is Asn.

18. The peptide of claim 17 wherein $R_{30}$ is $desR_{30}$, $R_{31}$ is $desR_{31}$ and $R_{32}$ is $desR_{32}$.

19. The peptide of claim 8 which is [D-Ala$^2$, Nle$^{27}$, Asn$^{28}$]-hGRF(1-29)NHEt.

20. The peptide of claim 8 which is [D-NMA$^2$, Nle$^{27}$, Asn$^{28}$]-hGRF(1-29)NHEt.

21. The peptide of claim 8 which is [D-NMA$^2$, Nle$^{27}$, Asn$^{28}$]-hGRF(1-32)-NH$_2$.

22. The peptide of claim 8 which is [D-NMA$^2$, Nle$^{27}$, Asn$^{28}$]-hGRF(1-29)NH$_2$.

23. The peptide of claim 8 which is [Nle$^{27}$, D-Asn$^{28}$]-rGRF(1-29)-NH$_2$.

24. The peptide of claim 8 wherein $R_1$ is substituted by N$^a$Me.

25. The peptide of claim 11 wherein $R_1$ is N$^a$MeTyr.

* * * * *

UNITED STATES PATENT AND TRADEMARK OFFICE
CERTIFICATE OF CORRECTION

PATENT NO. : 4,728,726
DATED : March 1, 1988
INVENTOR(S) : Jean E. F. Rivier et al.

It is certified that error appears in the above-identified patent and that said Letters Patent is hereby corrected as shown below:

Column 6, Line 31, After "bond" insert --$X^8$--

Column 8, Line 50, Change "TYyr" to --Tyr--

Column 11, Line 6, Change "Leu-His" to --Leu-Leu-His--

Column 14, Line 49, Change "pCl-phe," to --pCl-Phe,--

Column 14, Line 55, Change "Gin" to --Gln--

Column 14, Line 63, Delete "13"

Signed and Sealed this

Eighth Day of November, 1988

Attest:

DONALD J. QUIGG

*Attesting Officer*   Commissioner of Patents and Trademarks